(12) United States Patent
Choi et al.

(10) Patent No.: US 10,456,224 B2
(45) Date of Patent: Oct. 29, 2019

(54) METHOD FOR GUIDING DENTAL IMPLANT PLAN, APPARATUS FOR SAME, AND RECORDING MEDIUM THEREFOR

(71) Applicant: OSSTEMIMPLANT CO., LTD., Seoul (KR)

(72) Inventors: Kyoo Ok Choi, Seoul (KR); Tae Hwan Kim, Seoul (KR); Seung Yong Hwang, Seoul (KR); Seong Yun Lee, Bucheon-si (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 31 days.

(21) Appl. No.: 15/540,641

(22) PCT Filed: Dec. 4, 2015

(86) PCT No.: PCT/KR2015/013257
§ 371 (c)(1),
(2) Date: Jun. 29, 2017

(87) PCT Pub. No.: WO2016/108452
PCT Pub. Date: Jul. 7, 2016

(65) Prior Publication Data
US 2017/0360533 A1 Dec. 21, 2017

(30) Foreign Application Priority Data

Dec. 31, 2014 (KR) .................. 10-2014-0195216
Mar. 24, 2015 (KR) .................. 10-2015-0040799

(51) Int. Cl.
*A61C 13/00* (2006.01)
*A61C 8/00* (2006.01)
(Continued)

(52) U.S. Cl.
CPC ........... *A61C 13/0004* (2013.01); *A61C 8/00* (2013.01); *G06F 3/04842* (2013.01);
(Continued)

(58) Field of Classification Search
None
See application file for complete search history.

(56) References Cited

U.S. PATENT DOCUMENTS 8,221,121 B2   7/2012  Berckmans, III
9,508,106 B1 *  11/2016  Salmassy ............. A61C 8/0093
(Continued)

FOREIGN PATENT DOCUMENTS

CN          1678254      10/2005
CN          101822575     9/2010
(Continued)

OTHER PUBLICATIONS

International Search Report for International Application No. PCT/KR2015/013257, dated Apr. 14, 2016.
(Continued)

*Primary Examiner* — Idowu O Osifade
(74) *Attorney, Agent, or Firm* — Kile Park Reed & Houtteman PLLC

(57) ABSTRACT

The present invention relates to a method of guiding a dental implant treatment plan, a device and a recording medium therefore. The method of guiding a dental implant treatment plan according to the invention, by providing a guide to the area where the implant object is to be placed, the effects of reducing the complexity of the implant plan and decreasing procedure deviations depending on individual to individual can be achieved.

18 Claims, 9 Drawing Sheets
(3 of 9 Drawing Sheet(s) Filed in Color)

(51) Int. Cl.
*G06T 7/11* (2017.01)
*G06T 7/70* (2017.01)
*G06F 3/0484* (2013.01)
*G06T 7/00* (2017.01)

(52) U.S. Cl.
CPC .............. *G06T 7/0012* (2013.01); *G06T 7/11* (2017.01); *G06T 7/70* (2017.01); *G06T 2207/30036* (2013.01)

(56) References Cited

U.S. PATENT DOCUMENTS

| | | |
|---|---|---|
| 2010/0151417 A1 | 6/2010 | Nilsson et al. |
| 2011/0269104 A1 | 11/2011 | Berckmans, III et al. |
| 2013/0316298 A1 | 11/2013 | Ikegami et al. |

FOREIGN PATENT DOCUMENTS

| | | |
|---|---|---|
| CN | 103442645 | 12/2013 |
| JP | 2003-245289 | 9/2003 |
| KR | 10-0912973 | 8/2009 |
| KR | 10-2009-0124649 | 12/2009 |
| KR | 10-1190651 | 10/2012 |

OTHER PUBLICATIONS

Extended European Search Report for European Application No. 15875546, dated Jun. 22, 2018.

\* cited by examiner (a)

(b)

(a)

METHOD FOR GUIDING DENTAL IMPLANT PLAN, APPARATUS FOR SAME, AND RECORDING MEDIUM THEREFOR

FIELD

The present invention relates to a method of guiding a dental implant treatment plan, a device and a recording medium therefore. More specifically, the present invention relates to a method of dental implant treatment planning guide that provides a guide to dentist in software for the implant planning a device and a recording medium therefore.

BACKGROUND OF INVENTION

The implant is to replace a lost tooth, and the procedures to establish appropriate implant planning on implant insertion position and direction, size and type of implant is a crucial process for successful treatment.

Conventionally, the program user to perform implant treatment depends mainly on the experience and the sense to establish position of prosthesis such as the fixture, the abutment, virtual crown, and therefore the deviation of the implant planning is made by individual to individual so as to raise strong doubts concerning the reliability of the result of the implant treatment.

Also, the conventional software has not provided any guide for the establishment of the implant planning so for users to modify the implant plan repeatedly, which causes to increase the time required and the complexity of procedures for the implant planning. Therefore, a planning method that can guide a user is required to reduce the reliance on user experience and to simplify and decrease the time that takes for establishing the plan.

DETAILED DESCRIPTION OF THE INVENTION

Technical Challenge

An object of the present invention, which is to solve aforementioned problems of having a high dependence on user experience and taking a long time when planning implant treatment, is to provide a guide to dentist in software for the implant planning, and a device and a recording medium therefore.

The Solution of Invention

In order to achieve the above object, method for dental implant planning in accordance with one aspect of the present invention comprises the steps of detecting a region where a tooth has been lost based on a tooth image; calculating an implant area where an implant is to be placed in the region; and displaying the implant area on the teeth image by using a pre-determined mark.

In the method, the step of calculating the implant area comprises calculating the implant area by applying a boundary surface as a criteria, wherein the boundary surface is determined based on at least one of the elements among occlusal surfaces, adjacent teeth in the region where the tooth has been lost, gingiva, cortical bones, neural tubes, and a maxillary sinus.

The above method may further comprises receiving a selection of at least one implant area among the implant areas displayed on the teeth image by a user input unit; determining a position where a recommended implant object or a user preference implant object is inserted into the selected implant area; and displaying an image where the implant object has been inserted automatically in the determined position.

Also, in order to achieve the above object, the device for dental implant planning guide in accordance with another aspect of the present invention, comprises a lost region detection unit that detects a region where a tooth was lost based on a tooth image; an implant area calculation unit that calculates an implant area where an implant is to be placed in the region; and a planning guide providing unit that provides an implant planning guide by displaying the calculated implant position area on the teeth image.

In the device, the implant area calculation unit may calculate the implant area by applying a boundary surface as a criteria, and the boundary surface may be determined based on at least one of the elements among occlusal surfaces, adjacent teeth in the region where the tooth has been lost, gingiva, cortical bones, neural tubes, and a maxillary sinus.

Also, in the device, the implant area calculation unit calculates the implant area by setting first boundary surface, second boundary surface, and third boundary surface, and the first boundary surface is set based on a boundary between the left and right adjacent teeth of the region, the second boundary surface is set based on occlusal surface, and the third boundary surface is set based on position of neural tubes in lower jaw or maxillary sinus in upper jaw.

Meanwhile, the implant area calculation unit can calculate position of each of the implant objects comprising at least one among a fixture, an abutment, and the virtual crown.

To calculate each position for implant objects, the implant area calculation unit comprises: a virtual crown area calculation unit that calculates a virtual crown position area by setting the first boundary surface based on a boundary with the left and right adjacent teeth of the region, setting the second boundary surface based on occlusal surface, and setting the third boundary surface based on gingiva junction; an abutment area calculation unit that calculates an abutment position area by setting the first boundary surface based on a boundary with left and right adjacent teeth of the region, setting the second boundary surface based on gingiva junction and setting the third boundary surface based on the boundary of cortical bone; and a fixture area calculation unit that calculates a fixture position area by setting the first boundary surface based on a boundary with left and right adjacent teeth of the area, setting the second boundary surface based on a boundary of cortical bone, and setting the third boundary surface based on the position of neural tube in lower jaw or the position of maxillary sinus in upper jaw.

Or, the implant area calculation unit can comprise a virtual crown area calculation unit that calculates a virtual crown position area by setting the first boundary surface based on a boundary with the left and right adjacent teeth of the region, setting the second boundary surface based on occlusal surface, and setting the third boundary surface based on gingiva junction; an abutment area calculation unit that calculates an abutment position area by setting the first boundary surface based on a boundary with left and right adjacent teeth of the region, setting the second boundary surface based on gingiva junction and setting the third boundary surface based on the boundary of cortical bone; and a fixture area calculation unit that calculates a fixture position area by setting the first boundary surface based on a boundary determined by at least one criteria information among criteria distance information between adjacent teeth of the region and a fixture, criteria distance information between adjacent fixtures, criteria distance information between teeth of the region and center of a fixture, and criteria distance information between centers of adjacent fixtures, setting the second boundary surface based on a boundary of cortical bone, and setting the third boundary surface based on the position of neural tube in lower jaw or the position of maxillary sinus in upper jaw.

When calculating position for respective implant object as stated above, the virtual crown calculation unit and the abutment area calculation unit calculate each the virtual crown position area and the abutment position area by setting the fourth boundary surface based on a boundary between buccal side and lingual side of maximum convexity of the left and right adjacent teeth crown of the region, and the fixture area calculation unit calculates the fixture position area by setting the fourth boundary surface based on a boundary of buccal side and lingual side cortical bone to calculate the implant area in 3-dimensions.

On the other hand, the plan guide providing unit can display the implant position area separated by each implant object including at least one among a fixture, an abutment and a virtual crown.

In addition, the device may comprise an user input unit that receives the selection of at least one implant area among the implant areas displayed on the teeth image, and an implant planning unit that determines a position within the selected implant area through the user input unit, where recommended object or user preferred implant object is to be inserted automatically, wherein the planning guide providing unit displays an image where an implant object is inserted in the position determined by the implant planning unit.

The plan guide providing displays the arrangement of tooth icons coupling one-to-one to tooth area of the teeth image, but make a distinction between the display of the tooth icons coupled to the missing tooth area and the display of the tooth icons coupled to the existing tooth area in the arrangement, so it can improve intuitive insight and increase ease of operation for users.

In addition, the above stated object can be also achieved by a computer-readable recording medium storing a program to execute the method of dental implant planning.

The Effect of Invention

As stated above, according to the present invention, by providing a guide to the area that is the object to implant position, there are the effects of reducing the complexity of the implant plan and decreasing procedure deviations depending on users.

Also, according to the present invention, the user can increase the accuracy of treatment by providing the opportunity to verify the procedure itself during treatment.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF EXEMPLARY EMBODIMENTS

Figure 1:
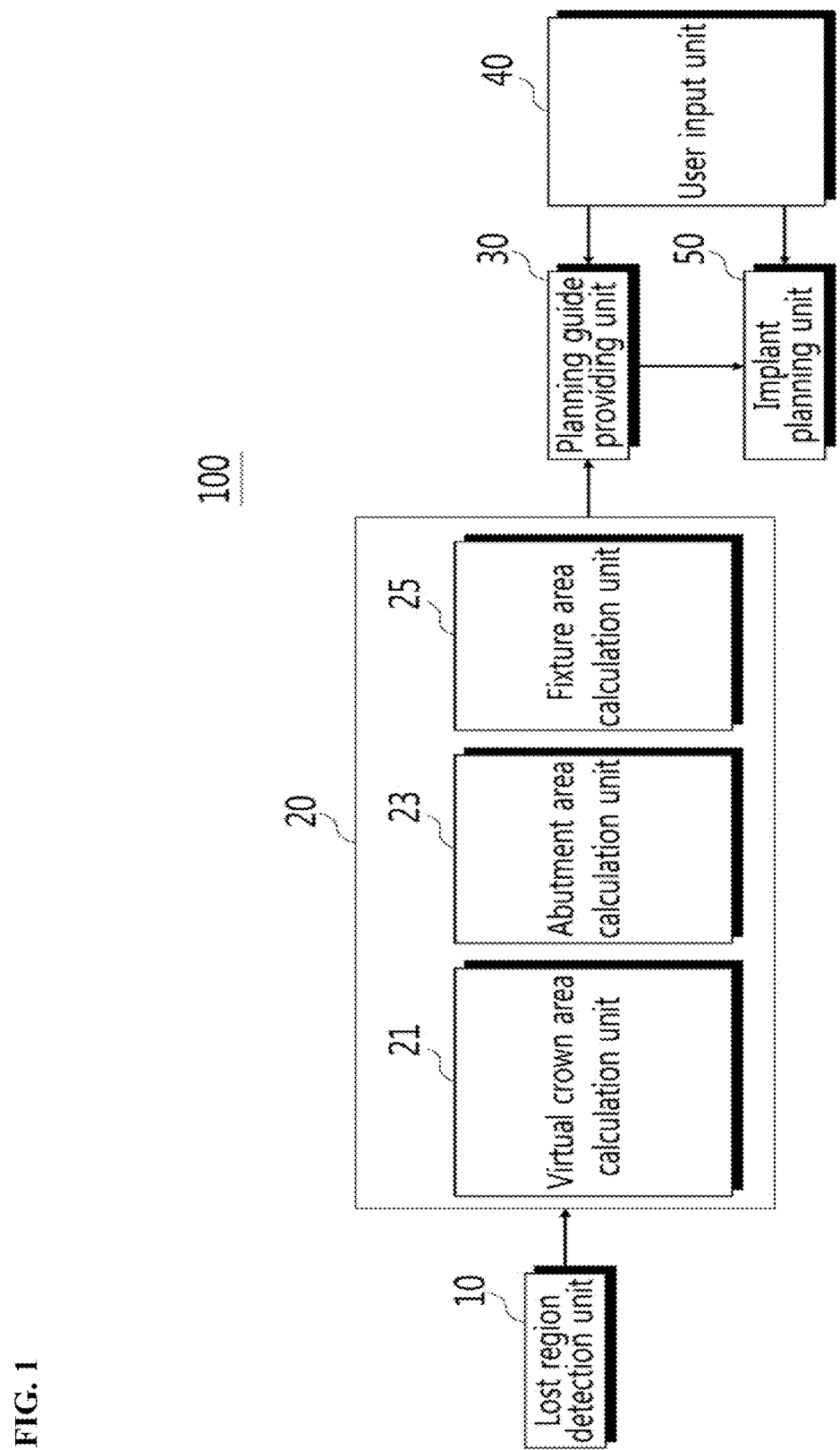
FIG. 1 is a block diagram for implant planning guide device according to an embodiment of the present invention.

Hereinafter, with reference to the accompanying drawings, preferred embodiments of the present invention will be described in detail. However, the explanation on the known functions and configurations that may obscure the subject matter of the present invention from the detailed description of the following description and from the accompanying drawings will be omitted. In addition, the same components throughout the drawings are referred to by the same reference numerals as possible which is to be noted.

The terms used in this specification and claims is not to be construed as limited to dictionary meanings, but can be defined and interpreted based on the meanings and concepts corresponding to technical aspects of the present invention in the principle that inventors define the terms appropriate to the concept of a term to describe his own invention in the best way. Therefore, the present embodiment and the configuration shown in the drawings and described in the specification is merely nothing but a preferable embodiment of the present invention, as not intended to represent all the technical concept of the present invention, so that it should be understood that many equivalents and varied modified embodiments of the present invention that can be made in the present application point.

FIG. 1 is a block diagram for the implant planning guide device 100 according to an embodiment of the present invention. Referring to FIG. 1, the implant planning guide device 100 comprises the lost region detecting unit 10, the implant area calculation unit 20, the planning guide providing unit 30, the user input unit 40 and the implant planning unit 50.

The lost region detecting unit 10 detects the region where the tooth has been lost in teeth image. Tooth lost region can be detected by extracting the upper and lower dental arch malicious trajectory and analyzing the extracted arch trajectory. For example, the lost region detecting unit 10 will be able to detect the tooth lost region on the dental arch trajectory with the various image analysis algorithm based on the gray scale value of the image.

The implant area calculation unit 20 calculates implant area where the implant is to be placed on the tooth lost region detected from the lost region detecting unit 10. Implant area, where the implant can be placed, means an area where the implant objects that form the implant, for example, a fixture, the abutment, and virtual crown can be placed. In this case, but also to calculate the implant area for all the detected tooth lost region, the actual implant placing area in the detected lost region is to be selected by the user and only the implant area in the selected implant placing area can be implemented to be calculated.

When placing an implant, it should be considered for harmonization of surrounding structures and organization and effects about masticatory movement or aesthetic elements. To this, the implant area calculation unit 20 can calculate the implant area on the basis of the boundary surface determined based on at least one of elements among the adjacent teeth of the teeth are lost region, gingiva, cortical bone, neural tube, and maxillary sinus. At this moment, when calculating implant area, the lost region is based on neural tube if the lost region exists in lower jaw or maxillary sinus if the lost region exists in upper jaw. For reference, occlusal surface is boundary surface that upper teeth and power teeth meets and form when shutting up the mouse, the gingiva means the pink style mucosal tissue covering the alveolar bone in the apical direction from the alveolar, the cortical bone is periodontal bone outermost regions, the hardest unit of the maxillary sinus, which means in the maxilla.

Meanwhile, calculating the implant position area is based on a criteria from boundary surface which is established through the position of the teeth, gingiva, cortical bone, neural tube, sinus, etc. adjacent to the lost region, as described above, further considering pre-stored information from users and a guide information about object placement position such as the type of each implant object, intraoral implant position of the area to be placed, a distance information between adjacent teeth and implant objects, a distance information by each adjacent implant, an implant object reference information, a placement relation information among implant objects etc. More explanation on this will be described in more detail below.

In addition, the implant area calculation unit 20 can calculate the position of the respective implant object or calculate the integrated implant area without dividing implant objects such as the fixture, the virtual crown, and so on that make up the implant. Like this, as the composition for calculating insertion position area by each implant object, the implant area calculation unit 20 can be divided into the virtual crown area calculation unit 21 which calculates the virtual crown position area, the abutment area calculation unit 23 which calculates an abutment position area, and the fixture area calculation part 25 which calculates a fixture position area. The implant area calculation part 20, to calculate positions for each object, can use each boundary surface for each object.

The implant area calculation unit 20, not only can calculate implant area in a 2-dimensions based on the left and right boundary surfaces and upper and lower boundary surfaces only, but can calculate in 3-dimensions by applying a front and rear boundary surface by one axis, that is the buccal-lingual boundary in addition.

The planning guide providing unit 30 displays the implant area calculated by the implant area calculation unit 20 on the tooth image. Besides, the planning guide providing unit 30 displays a variety of images to provide guidance to the user on the implant planning process, including the user interface image representing the tooth lost region graphically by using the tooth icon. For this purpose, the planning guide providing unit 30 can be implemented using various display means for displaying images according to the implant planning process.

The user input unit 40 receives the selection from user for the implant area in the area displayed by the planning guide providing unit 30, and receives a variety of information required in the implant planning process.

The implant planning unit 50 determines the implant position area in the implant area displayed on the teeth image where the implant object is to be inserted automatically, wherein the implant object is preferred by user or recommended in the selected implant position area via the user input unit 40. Correspondingly, the planning guide providing unit 30 displays an image of the implant object inserted in the implant auto-insertion area which is determined by the implant planning section 50. Besides the above stated decision of implant insertion position area, the implant planning unit 50 performs the processes in the overall planning and implant planning modifications.

Figure 2:
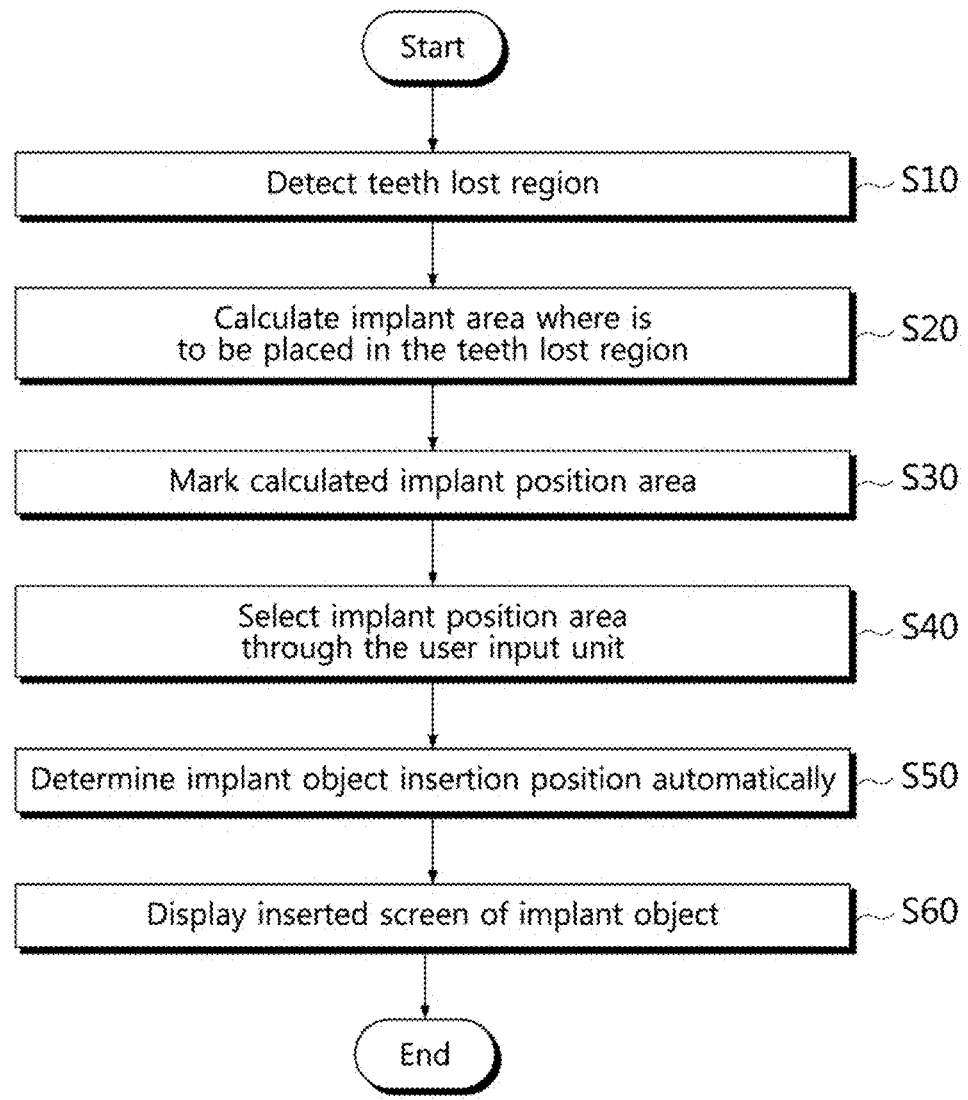
FIG. 2 is a flowchart illustrating procedures of providing the implant treatment planning method according to an embodiment of the present invention.

FIG. 2 is a flowchart showing the implant planning guide method according to an embodiment of the present invention. Hereinafter, referring to FIG. 2, the organic behavior of the constituent of implant planning guide device 100 will be explained.

The lost region detecting unit 10 detects the region where the tooth has been lost in teeth image in step S10. Lost area detection can be detected by extracting upper and lower dental arch in the trajectory tooth image and analyzing the extracted trajectory arch. The planning guide providing unit 30 displays the position of the detected lost region with coupled tooth icon arrangement, which can help the user's intuitive understanding and ease of operation.

Figure 3:
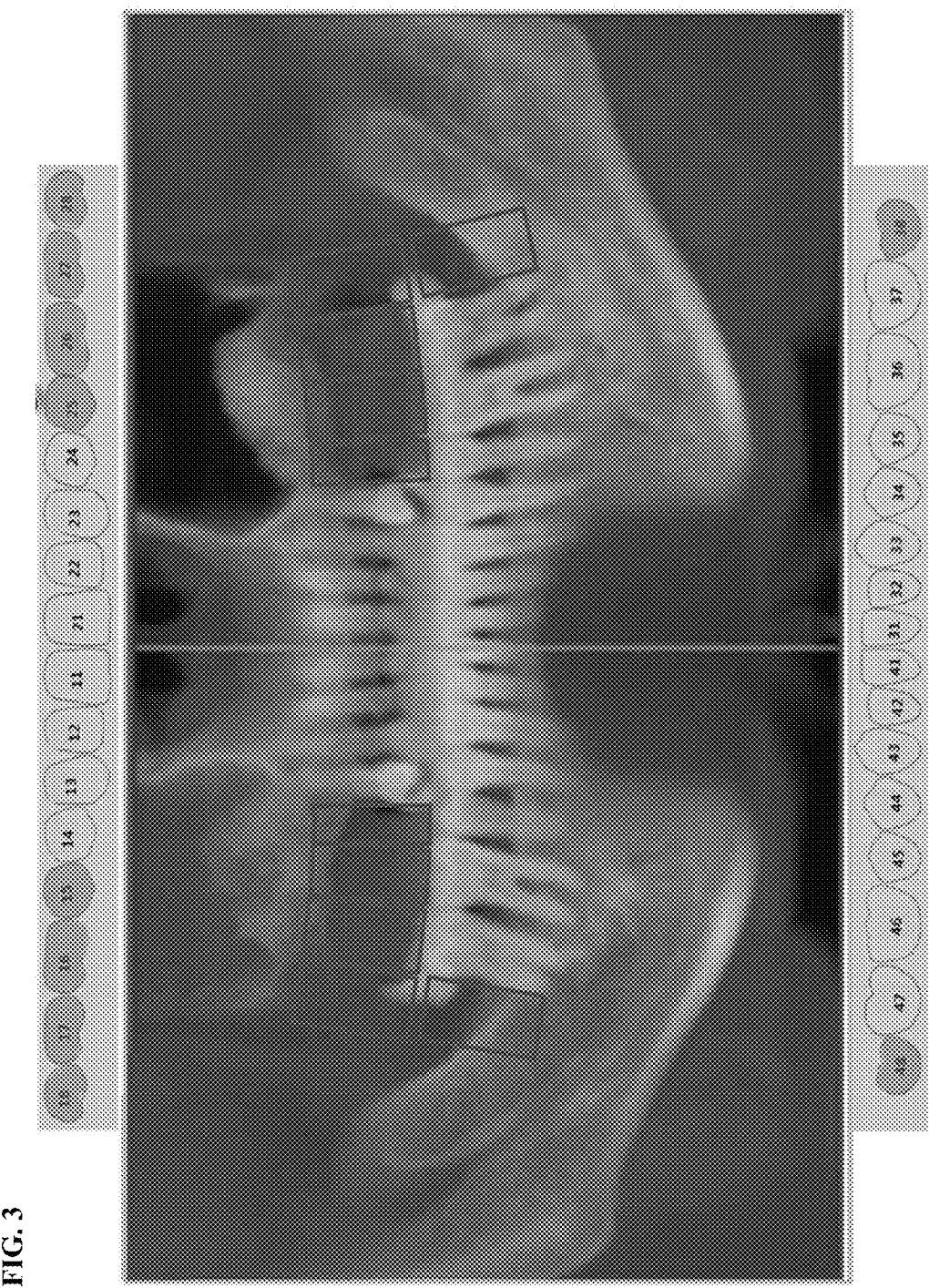
FIG. 3 illustrates an example of a screen displaying detected teeth lost region and the icon coupled to the region.

FIG. 3 illustrates an example of a screen displaying detected teeth lost region and the icon coupled to the region;

Referring to FIG. 3, the teeth icon arrangement which is one-to-one coupled with the tooth area in the panorama image is displayed, and the tooth number is given to each tooth icon. The planning guide providing unit 30 make a distinction between the display of the tooth icons with tooth number coupled to the missing tooth area and the display of the tooth icons coupled to the existing tooth area in the arrangement with marker such as different color, brightness, tooth icon, etc. which helps user intuitively grasp the teeth lost region. Furthermore, in the case due to problems of resolution or clarity the user may also experience difficult to distinguish or select the specific teeth in the teeth image, when selecting or operating the icon corresponding to the teeth the planning guide proving unit 30 can perform for the tooth area corresponding the icon on the tooth image, which increases the user's convenience.

For reference, the teeth icons shown in FIG. 3, which is exemplary shape, may be implemented in a variety of shapes such as including tooth root.

When the detection of the tooth lost region is made, the implant area calculation unit 20 calculates the implant area based on the boundary surface which is determined based on a variety of factors and information for tooth lost region selected through the user input unit 40 or the detected teeth lost region in step S20.

Figure 4:
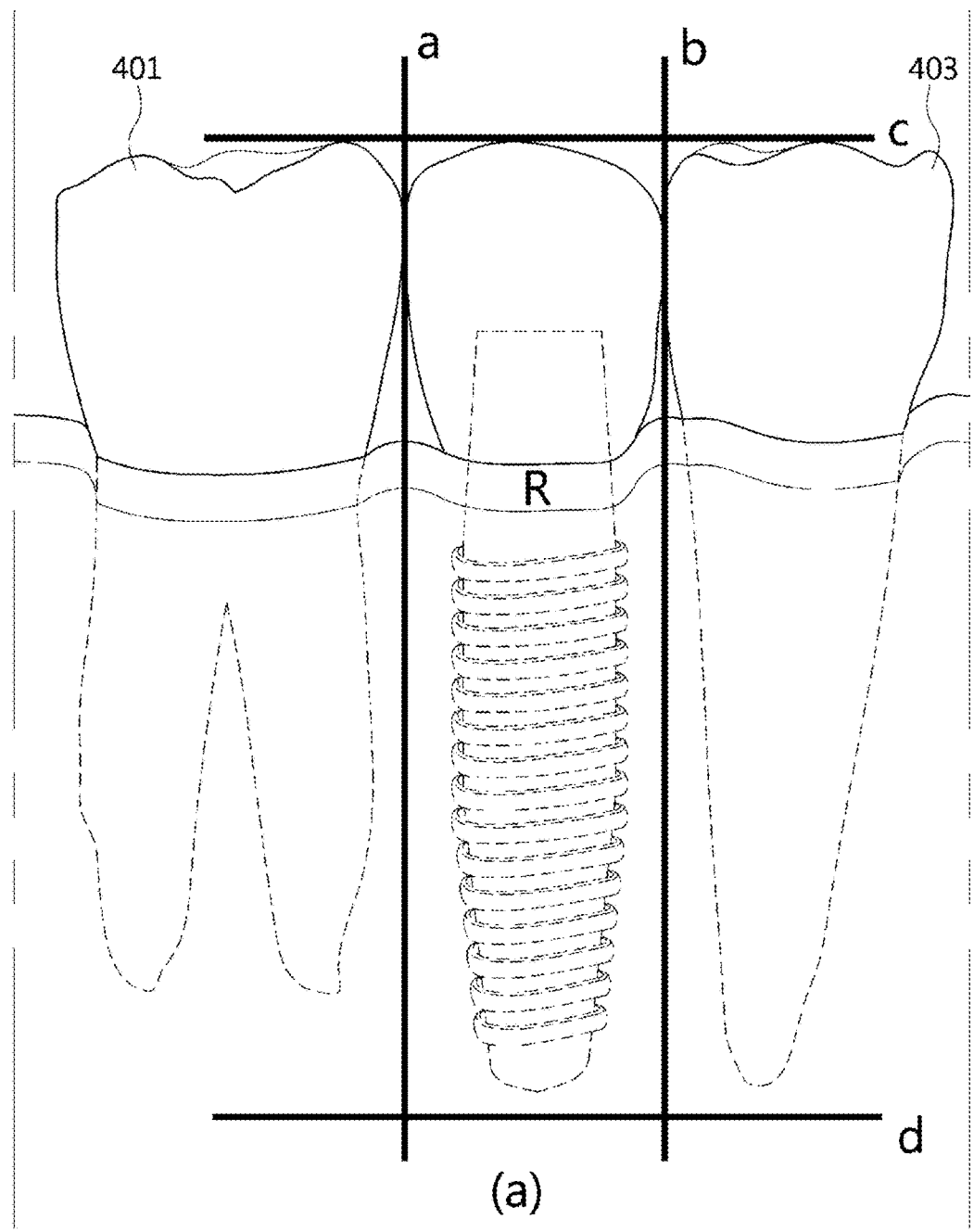
FIG. 4 and FIG. 5 are drawings to explain an example of calculating the implant position area.
Figure 5:
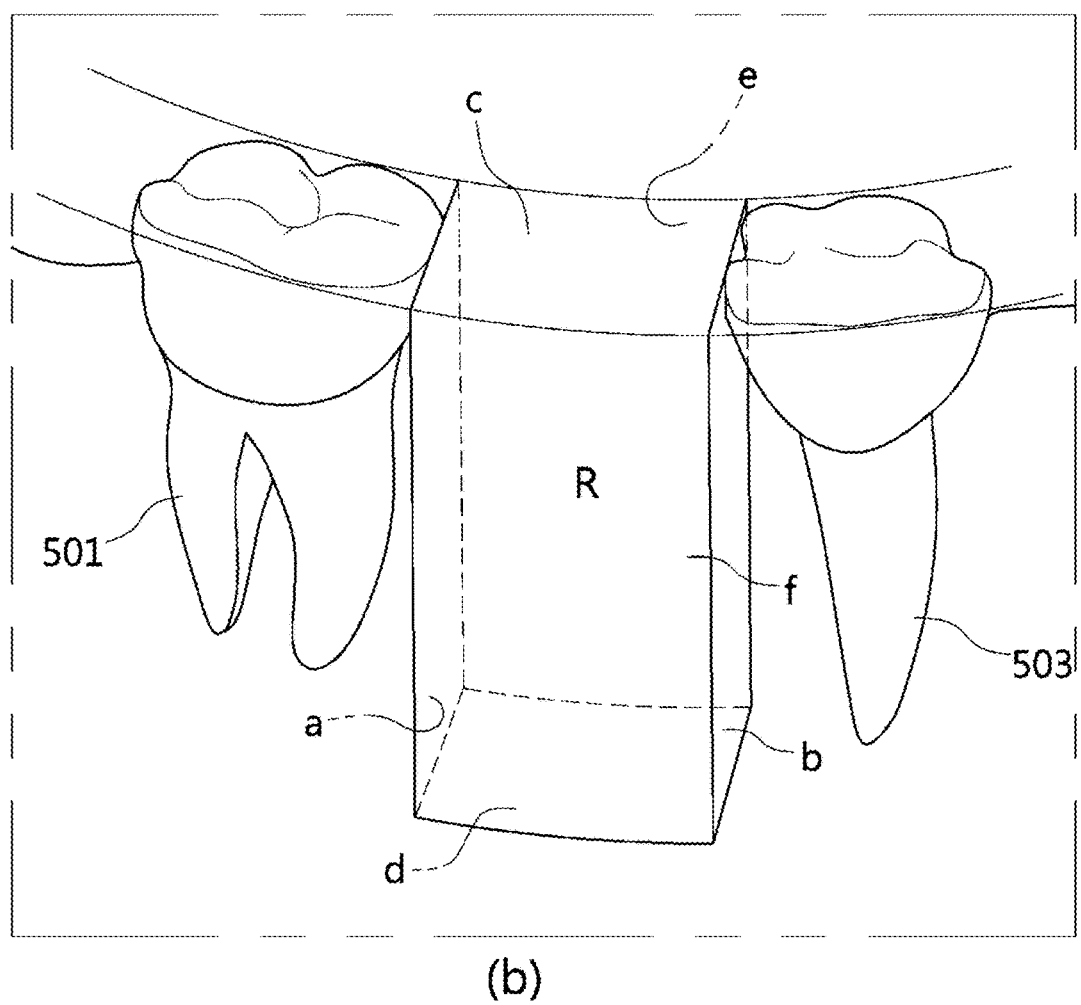

FIG. 4 and FIG. 5 are drawings to explain an example of calculating the implant position area;

First, referring to FIG. 4, the implant area calculation unit 20 sets the first boundary surface (a, b) based on the left and right boundaries with adjacent teeth (401, 403) in the tooth lost region, sets the second boundary surface (c) based on the occlusal surface, and sets the third boundary surface (d) based on the position of neural tube in lower jaw or the position of maxillary sinus in upper jaw to calculate the implant area (R).

On the other hand, the implant area calculation unit 20 follows implant area calculation basically as stated above. However, it can get some information of the area criteria through the user input unit 40 in advance, apply the input the area criteria to the calculated implant area as stated above, and to calculate the final implant area through the adjustment.

In addition, basically based on the calculation basis of the implant area as stated above, it can apply the position of the tooth lost region and the type of the inserted fixture and adjust it by predetermined length from the boundary surface to calculated the final implant area. For example, when teeth lost area is in position of the molars or premolars, in consideration of the characteristics according to the teeth position, the degree of the adjustment from the boundary surface may be applied differently to calculate the final implant area.

The implant area calculating unit 20 may extract the left and right boundary (a, b) and the upper and lower boundary surfaces (c, d) and calculate the implant area(R) in 2-dimensions in FIG. 4. However, it can comprise the 4th boundary surface as depicted in FIG. 5 and calculate the implant area(R) in 3-dimensions.

In FIG. 5, the implant area calculating unit 20 extracts the fourth boundary (e, f) based on a boundary surface between buccal side and lingual side of maximum convexity of the left and right adjacent teeth crown of the region and adds one axis information to the implant area calculated in FIG. 4 to show an example of calculating the implant area (R) in 3-dimensions. According to FIG. 5, the implant area (R) can be defined as a cube, and at this time, the left and right boundary surfaces (a, b) are each side of the cube, the upper and lower boundary surfaces (c, d) are top and bottom of each cube, buccal/lingual boundary surface (e, f) corresponds to the front and back surface of each of the cube.

Meanwhile, in FIG. 4 and FIG. 5, the example was shown for calculating an integrated implant area (R) without considering respective implant object, the implant area position unit 20 can calculate implant area for the respective implant object that forms the implant such as a fixture, a virtual crown, an abutment, respectively.

Figure 6:
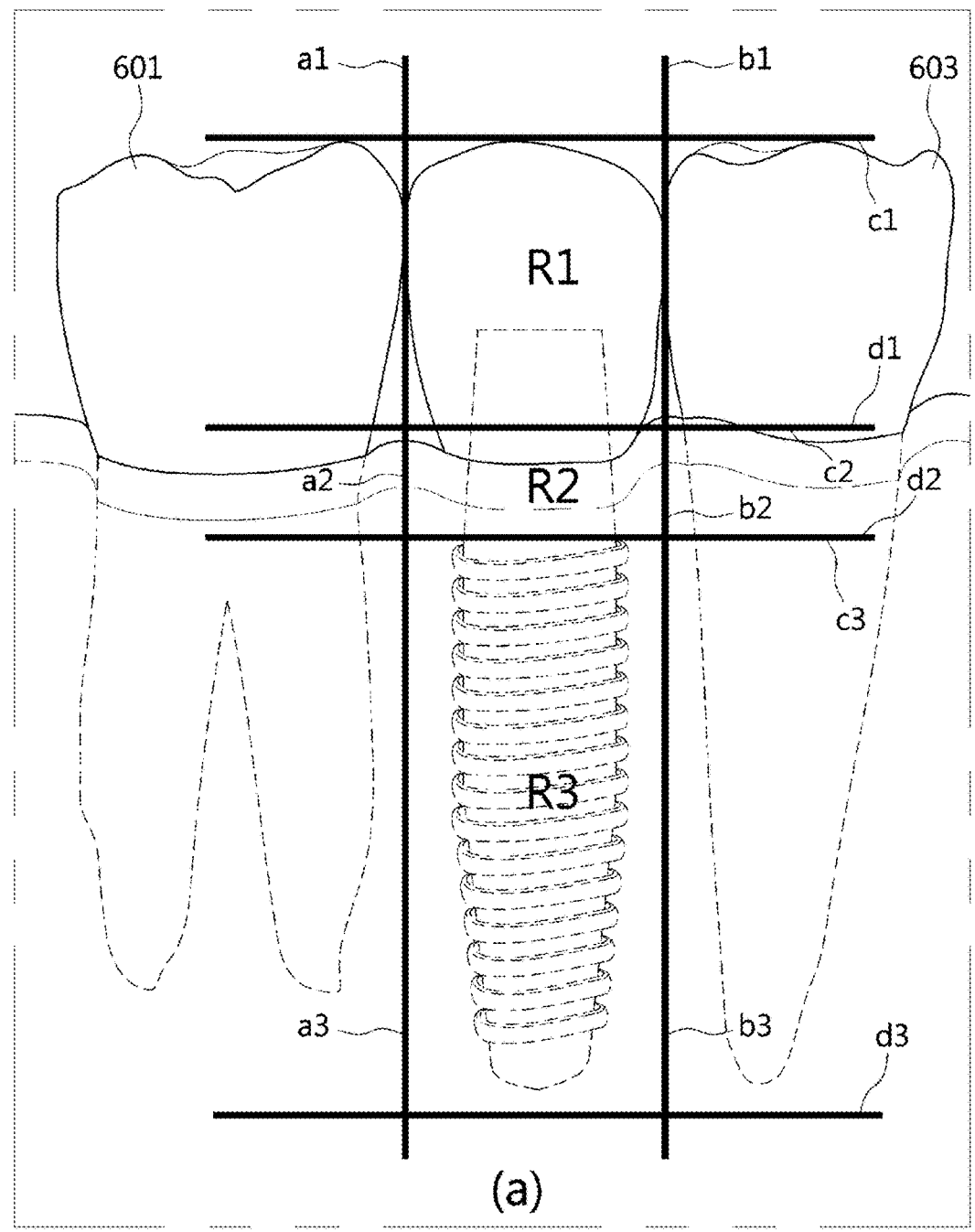
FIG. 6 is a drawing to explain an example of the reference for calculating the implant area corresponding to each implant object.

FIG. 6 is a drawing to explain an example of the reference for calculating the implant area corresponding to each implant object. Hereinafter, referring to FIG. 6, an example for calculating implant area by each object will be considered. At this time, orders of the each object whose implant area is calculated may be changed.

Looking at the example for calculating a virtual crown position area according to the virtual crown area calculation unit 20, the virtual crown calculation unit 21 sets the first boundary surface (a1, b1) based on the boundary between the left and right adjacent teeth (601, 603) of the lost region, sets the second boundary surface (c1) based on the occlusal surface, and sets the third boundary surface (d1) based on the boundary of the adjacent gingiva in the teeth lost region to calculate the position area of the virtual crown (R1).

The abutment area calculation unit 23 sets the first boundary surface (a2, b2) based on boundary surface with left and right adjacent teeth (501, 603), sets the second boundary surface (c2) based on the boundary of adjacent gingiva in the teeth lost region, and sets the third boundary surface (d2) based on the boundary of the cortical bone to calculate the abutment position area (R2).

The fixture area calculation unit 25 sets the first boundary surface (a3, b3) based on the boundary with the left and right adjacent teeth (601, 603) in the lost region, sets the second boundary surface (c3) based on the boundary of the cortical bone, and sets the third boundary surface (d3) based on the position of neural tube in lower jaw or the position of maxillary sinus in upper jaw, to calculate the fixture position area (R3).

Meanwhile, as depicted in FIG. 6, the implant area (R1, R2, R3) can be calculated in 2-dimensions for each implant object, but as described above referring to FIG. 5, the implant position area (R1, R2, R3) can be calculated in 3-dimensions for each implant object.

For example, the virtual crown area calculation unit 21 and the abutment area calculation unit 23 can calculate the virtual crown and abutment position area (R1, R2) in 3-dimensions by setting the fourth boundary based on a boundary between buccal side and lingual side of maximum convexity of the left and right adjacent teeth crown of the region. Also, the fixture area calculation unit 25, by setting the fourth boundary based on the cortical boundary of the buccal side and lingual side, can calculate the fixture position area (R3) in 3-dimensions.

Figure 7:
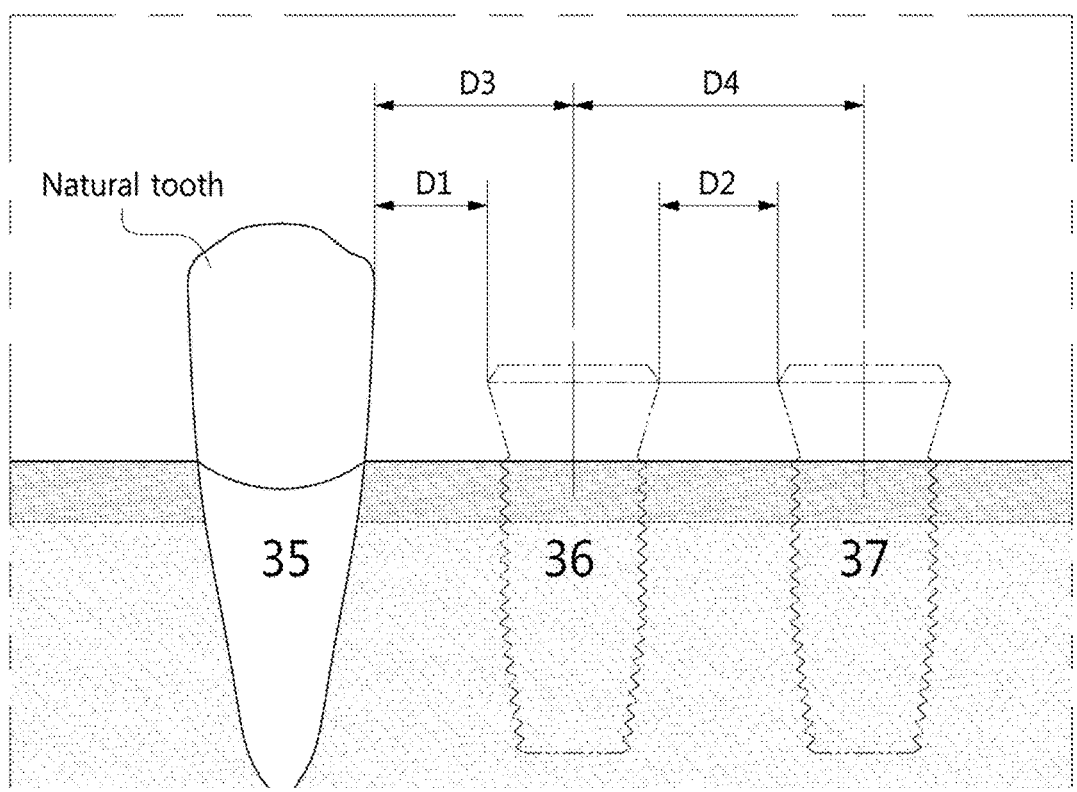
FIG. 7 is a drawing to explain another example for calculating the fixture position area.

Referring to FIG. 6 in the above example, the fixture position area 25 sets the first boundary surface (a3, b3) based on boundary with the left and right adjacent teeth (601, 603) in the lost region to calculate the fixture position area, but in consideration that the position where the fixture is implanted is narrower than the width of the position area (R1) of the virtual crown, the fixture position area (R3) can be calculated by reflecting the specific information about the fixture position as illustrated in FIG. 7.

FIG. 7 is a drawing to explain another example for calculating the fixture position area.

Referring to FIG. 7, if the tooth 36 and tooth 37 has been lost, the fixture area calculation unit 25 saves in advance reference information and set the first boundary surface(a3, b3) based on boundary determined from the reference information to calculate the fixture position area(R3), wherein the reference information comprises adjacent the tooth (tooth 35) and the reference distance between the fixture of the teeth loss regions (36 teeth area) (D1), an adjacent fixture between the reference distance (D2), the teeth loss area adjacent teeth (36 teeth area) (35 teeth) and the reference distance between the fixture center (D3), the reference distance between the adjacent fixture center (D4), etc. For example, as an example of the reference information, by applying D1 of 3.5 mm, D2 of 4 mm, D3 of 5.5 mm, D4 of 8 mm, the fixture position area may be calculated. Above reference information is one example, and as the stored reference information recommended procedure guide information though common in the industry or input data demonstrated by users empirically may be used, and the reference information can be set respectively depending on the teeth position and the fixture type applied.

The planning guide providing unit 30 marks the implant area calculated in 2 or 3 dimensions through the above stated steps on the teeth image with using a predetermined mark in step S30.

Figure 8:
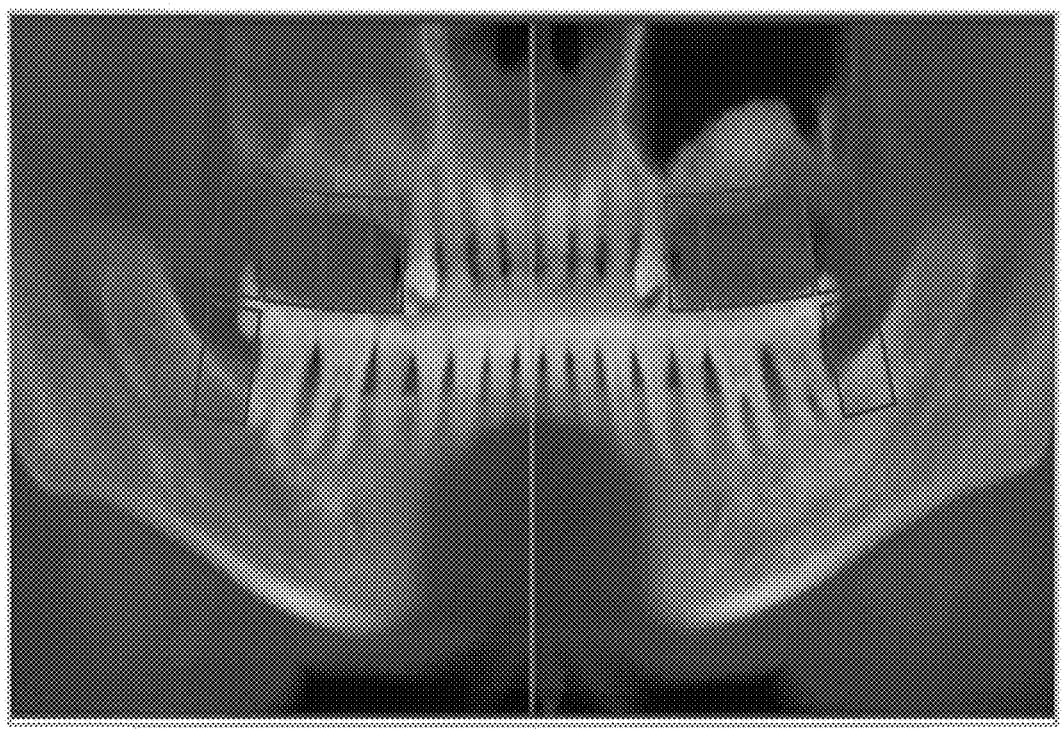
FIG. 8 and FIG. 9 is an example of a screen displaying the calculated implant area.
Figure 9:
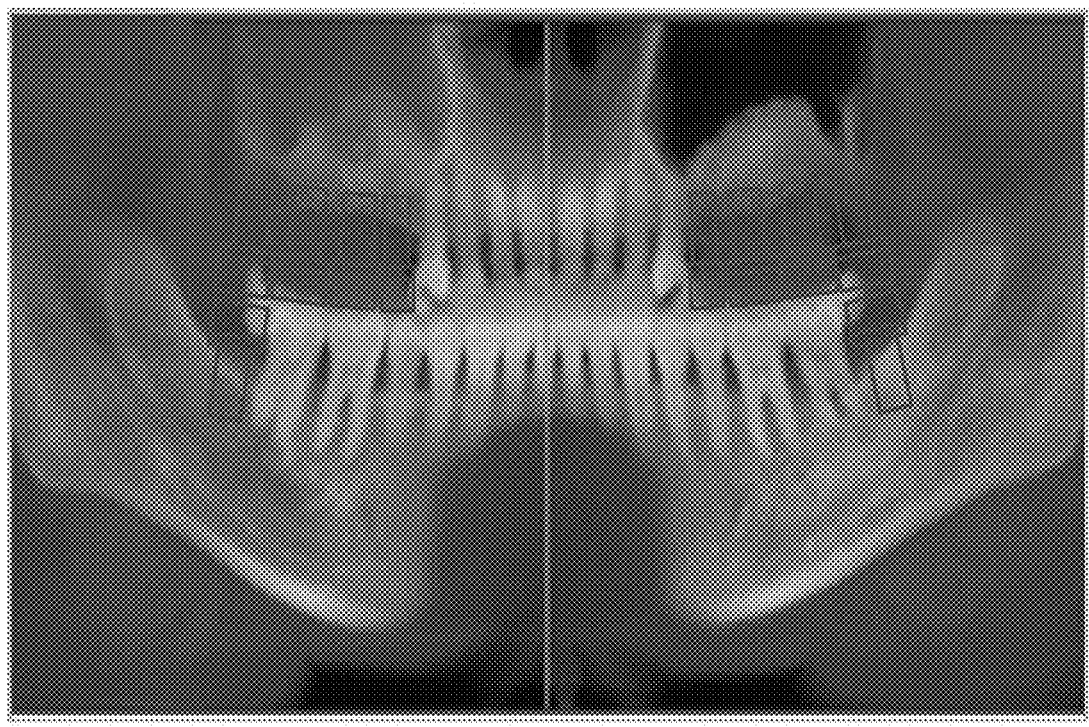

FIG. 8 and FIG. 9 is an example of a screen where the planning guide providing unit 30 displays the calculated implant area.

The planning guide providing unit 30 can display the implant area integrally for all the implant objects as depicted in FIG. 8 or can display the each implant area for the respect implant object as depicted in FIG. 9. On the other hand, in case of displaying integrally implant area as depicted in FIG. 8, the implant area of the implant object selected by dragging can be displayed, separated from unselected implant object.

Meanwhile, the planning guide providing unit 30 can display the calculated implant area as shown FIG. 8 and FIG. 9 in 2-dimensions, or display the calculated implant area depending on the user's selection or as needed in 3-dimensions. In this case, FIG. 8 and FIG. 9 illustrate the screen which the calculated implant area displays in 2-dimensions, when displaying 3-dimensional implant position area, it can be displayed in 3-dimensional image such as CT image, scan image etc.

When the implant area is displayed, it receives the implant position area where implant is to be placed through the user input unit 40.

When selection of one or a plurality of implant area is made, the implant planning unit 50 determines the position where the recommended implant object or user's preferred implant object, is inserted automatically in step S50. At this time, information about recommended implant object and user's preferred implant object can be pre-stored, or receiving recommended object information whenever determining insertion position from outside, or receiving a preferred object information by a user.

On the other hand, the implant planning unit 50 can determine auto-inserted position based on pre-stored information entered in advance or the guide information about the object insertion position comprising a kind of each implant object, the position of the selected area, the distance information between adjacent teeth and objects, the reference information by each adjacent implant object, the reference information depending on insertion position, the insertion information among implant objects.

For example, it is principle to determine the auto-inserted position within the area shown by the planning guide providing unit 30, specific auto-insertion position can be determined depending on the length, and specific auto-inserted position can be determined differently according to the type of the object, the teeth, e.g. the molars, premolars. Furthermore, it can be determined to reflect the standard guide information according to each object insertion position and preferred position information according to user's experience, such as the fixture is placed in the center of the imaginary crown, the abutment is placed in a position to endure the weight of a virtual crown.

The planning guide providing unit 30 displays the image with the inserted implant object in position corresponding to the implant object auto-insertion position determined by the implant planning unit 50. In addition, the planning guide providing unit 30, after displaying the image with the inserted implant object, displays the information on the inserted implant and its inventory status by interlocking with ERP(Enterprise Resource Plan) program, which will be able to proceed the implant plan process afterward on the basis of this.

Meanwhile, the steps described above may be properly added or modified as needed to be applied. For example, the implant planning unit 50 can provide the user with an automatic insertion mode of the implant object alternatively, and if the user did not select the automatic insertion mode, the user can insert implant object directly in the area marked by the planning guide providing unit 30 through the user input unit 40, and it may be implemented to provide notification if exceeding the area according to the automatic insertion criteria, such as the example described.

On the other hand, the implant planning unit 50 can provide the correction function for the object inserted automatically or manually in response to user input through the user input unit 40. In this case, but also to modify each by implant object, it can increase user's convenience by modifying the grouped implant objects together optionally. Also, the implant planning unit 50, when invading structure which should not be intruded such as sinus neural tube or maxillary sinus etc. during the modification of an object or modified beyond the area of the placement guide information stored in advance, may provide notification about this.

On the other hand, the implant guide method according to an embodiment of the present invention is written in a program that can be run on the computer and is implemented in a variety of recording medium such as magnetic storage media, optical recording media, digital storage media.

As can be seen from the above description, the implant guide device 100 according to the embodiment of the invention, the method, and the recording medium, the implant insertion position, which was determined only depending on user's experience and knowledge, can draw various factors within oral as standard boundary applied, can reduce the deviation of the procedure by providing guide information about it by providing guide information about this, so that a user can also provide a means to verify the procedure itself in the process.

Implementations of the various techniques described herein area digital electronic circuitry, or computer hardware, firmware, software, or may be implemented in a combination of them. Implementations can be implemented by a data processing device, for example, a programmable processor, a computer, or for processing by the operation of a plurality of computers, or to control the operation, the computer program product, i.e. the information carrier, for example, machine-readable apparatus (computer readable medium) or a radio signal. The computer program as stated above can be recorded in a programming language of any type, including a substituted or interpret compiled language, as a stand-alone program or as a module, component, subroutine, or in the computing environment, it may be deployed in any form, including as appropriate, including the use of other units. Computer program can be distributed across one or more computer or a number of sites to be processed on multiple computers at one site, and can be connected by a communication network.

Processors suitable for the processing of the computer program comprise as an example, includes both general and special purpose microprocessors, and more than one processors of any kind of digital computer. Generally, a processor may receive commands or data from read-only memory or random-access memory or both. The computer can include more than one memory device saving at least one processor and commands and data which executes commands. For example, it includes magnetism, magnetic-optical disks, or optical disks, or transmitting this data or combining both, or it can receive or transmit data or combine both. Information carriers appropriate for specifying computer program commands or data as an example, semiconductor memory device, for example, includes hard disks, floppy disks, and magnetic tape, such as magnetic media, CD-ROM (Compact Disk Read Only Memory), DVD (Digital Video disk) and the like optical recording media, floptical disk, such as magneto-optical media, ROM (Read Only Memory), RAM (Random Access memory), comprises a flash memory, EPROM (Erasable Programmable ROM), EEPROM (Electrically Erasable Programmable ROM) etc. Processor and memory can be added or included by special purpose logic circuitry.

The present description herein includes details a number of specific implementations, but it cannot be understood as limited for any invention or scope for patent claims, rather to be understand as explanation about featuring specific implementation of specific invention. The specific features of the present description in context of each implementation herein can be implemented in combination in a single embodiment. Conversely, it also can be implemented in a plurality of embodiments with different features, any suitable sub-combination or separately described in the context of a single embodiment. Furthermore, the features can be combined as specific combinations or described as claimed in early, but one or more features from claimed combinations can be excluded from the combination in some cases, the claimed combination can be changed as sub-combination or its modifications.

Likewise, although it describes operations as particular order, it cannot be understood that performing those operations as the specific or sequential order described to achieve desired results or being performed for all described operations. In certain case, multi-tasking and parallel processing can be advantageous. In addition, separation of various system components in the embodiments described above should not be understood to require in any embodiment such a separation, the described program components and systems are generally integrated together in a single software product or be packaged into multiple software products number that should be understood.

On the other hand, the embodiments of the invention disclosed in the specification and drawings are not presented merely a specific example for clarity and are not intended to limit the scope of the invention. It addition to the embodiments disclosed herein another modification based on the technical ideas of the invention are possible embodiments, it will be apparent to those of ordinary skill in the art.

What is claimed is:

1. A method of implant planning guide, comprising:
   detecting a region where a tooth has been lost based on a tooth image;
   calculating an implant area where an implant is to be placed in the region; and
   displaying the implant area on the teeth image by using a pre-determined mark indicating boundaries of the implant area,
   wherein the implant area is displayed separately for each of the implant objects which are parts of the implant, or the implant area is displayed integrally for all the implant objects,
   wherein in case that the implant area is displayed integrally for all the implant objects, the implant area of the implant object selected by a user is separately displayed from that of the others.

2. The method according to claim 1,
   wherein calculating the implant area comprises calculating the implant area by applying a boundary surface as a criteria, and
   wherein the boundary surface is determined based on at least one of the elements among occlusal surfaces, adjacent teeth in the region where the tooth has been lost, gingiva, cortical bones, neural tubes, and a maxillary sinus.

3. The method according to claim 1, further comprising:
   receiving a selection of at least one implant area among the implant areas displayed on the teeth image by a user input unit,
   determining a position where a recommended implant object or a user preference implant object is inserted into the selected implant area, and
   displaying an image where the implant object has been inserted automatically in the determined position.

4. A device for dental implant planning guide including at least a processor, comprising:
   a lost region detection unit that detects a region where a tooth was lost based on a tooth image,
   an implant area calculation unit that calculates an implant area where an implant is to be placed in the region, and
   a planning guide providing unit that provides an implant planning guide by displaying the calculated implant position area on the teeth image by using a pre-determined mark indicating boundaries of the implant area,
   wherein the planning guide providing unit displays the implant area separated for each of the implant objects which are parts of the implant, or displays the implant area integrally for all the implant objects,
   wherein in case that the planning guide providing unit displays the implant area integrally for all the implant objects, the implant area of the implant object selected by a user is separately displayed from that of the others.

5. The device for dental implant planning guide according to claim 4,
   wherein the implant area calculation unit calculates the implant area by applying a boundary surface as a criteria, and
   wherein the boundary surface is determined based on at least one of the elements among occlusal surfaces, adjacent teeth in the region where the tooth has been lost, gingiva, cortical bones, neural tubes, and a maxillary sinus.

6. The device for dental implant planning guide according to claim 4,
   wherein the implant area calculation unit calculates the implant area by setting first boundary surface, second boundary surface, and third boundary surface, and
   wherein the first boundary surface is set based on a boundary between the left and right adjacent teeth of the region, the second boundary surface is set based on occlusal surface, and the third boundary surface is set based on position of neural tubes in lower jaw or maxillary sinus in upper jaw.

7. The device for dental implant planning guide according to claim 6,
   wherein the implant area calculation unit calculates the implant area in 3-dimensions by setting the fourth boundary based on boundary between buccal side and lingual side of maximum convexity of the left and right adjacent teeth crown of the region.

8. A device for dental implant planning guide according to claim 4,
   wherein the implant area calculation unit calculates position of each of the implant objects comprising at least one among a fixture, an abutment, and the virtual crown.

9. The device for dental implant planning guide according to claim 4,
   wherein the implant area calculation unit comprises,
   a virtual crown area calculation unit that calculates a virtual crown position area by setting the first boundary surface based on a boundary with the left and right adjacent teeth of the region, setting the second boundary surface based on occlusal surface, and setting the third boundary surface based on gingiva junction;
   an abutment area calculation unit that calculates an abutment position area by setting the first boundary surface based on a boundary with left and right adjacent teeth of the region, setting the second boundary surface based on gingiva junction and setting the third boundary surface based on the boundary of cortical bone; and
   a fixture area calculation unit that calculates a fixture position area by setting the first boundary surface based on a boundary with left and right adjacent teeth of the area, setting the second boundary surface based on a boundary of cortical bone, and setting the third boundary surface based on the position of neural tube in lower jaw or the position of maxillary sinus in upper jaw.

10. The device for dental implant planning guide according to claim 4,
wherein the implant area calculation unit comprises,
a virtual crown area calculation unit that calculates a virtual crown position area by setting the first boundary surface based on a boundary with the left and right adjacent teeth of the region, setting the second boundary surface based on occlusal surface, and setting the third boundary surface based on gingiva junction;
an abutment area calculation unit that calculates an abutment position area by setting the first boundary surface based on a boundary with left and right adjacent teeth of the region, setting the second boundary surface based on gingiva junction and setting the third boundary surface based on the boundary of cortical bone; and
a fixture area calculation unit that calculates a fixture position area by setting the first boundary surface based on a boundary determined by at least one criteria information among criteria distance information between adjacent teeth of the region and a fixture, criteria distance information between adjacent fixtures, criteria distance information between teeth of the region and center of a fixture, and criteria distance information between centers of adjacent fixtures, setting the second boundary surface based on a boundary of cortical bone, and setting the third boundary surface based on the position of neural tube in lower jaw or the position of maxillary sinus in upper jaw.

11. The device for dental implant planning guide according to claim 9,
wherein the virtual crown calculation unit and the abutment area calculation unit calculate each the virtual crown position area and the abutment position area by setting the fourth boundary surface based on boundary between buccal side and lingual side of maximum convexity of the left and right adjacent teeth crown of the region, and the fixture area calculation unit calculates the fixture position area by setting the fourth boundary surface based on a boundary of buccal side and lingual side cortical bone to calculate the implant area in 3-dimensions.

12. A device for dental implant planning guide according to claim 4, further comprising:
an user input unit that receives the selection of at least one implant area among the implant areas displayed on the teeth image; and
an implant planning unit that determines a position within the selected implant area through the user input unit, where recommended object or user preferred implant object is to be inserted automatically,
wherein the planning guide providing unit displays an image where an implant object is inserted in the position determined by the implant planning unit.

13. The device for dental implant planning guide according to claim 12,
wherein the implant planning unit determines the auto-inserted position within the implant area,
wherein the implant area is calculated based on user input information and pre stored criteria information comprising at least one among criteria distance information between the implant object and adjacent tooth, criteria distance information between the same kinds of the adjacent implant objects, reference information on the implant object for the implant area, and insertion-relation information of the implant objects,
wherein the implant objects comprise a fixture, abutment, and virtual crown.

14. The device for dental implant planning guide according to claim 4,
wherein the planning guide unit displays the arrangement of tooth icons coupling one-to-one to tooth area of the teeth image, and make a distinction between the display of the tooth icons coupled to the missing tooth area and the display of the tooth icons coupled to the existing tooth area in the arrangement.

15. A non-transitory computer-readable recording medium for storing a program to execute the method of dental implant planning guide according to claim 1.

16. A non-transitory computer-readable recording medium for storing a program to execute the method of dental implant planning guide according to claim 2.

17. A non-transitory computer-readable recording medium for storing a program to execute the method of dental implant planning guide according to claim 3.

18. The device for dental implant planning guide according to claim 10,
wherein the virtual crown calculation unit and the abutment area calculation unit calculate each the virtual crown position area and the abutment position area by setting the fourth boundary surface based on boundary between buccal side and lingual side of maximum convexity of the left and right adjacent teeth crown of the region, and the fixture area calculation unit calculates the fixture position area by setting the fourth boundary surface based on a boundary of buccal side and lingual side cortical bone to calculate the implant area in 3-dimensions.

* * * * *